(12) United States Patent
Cheng et al.

(10) Patent No.: US 10,632,285 B2
(45) Date of Patent: Apr. 28, 2020

(54) CONTROL MECHANISM FOR MEDICAL DEVICE

(71) Applicant: Gyrus ACMI, Inc., Southborough, MA (US)

(72) Inventors: Ming J. Cheng, Southborough, MA (US); Allen Palmer, Southborough, MA (US); Yoshinari Okita, Southborough, MA (US)

(73) Assignee: Gyrus ACMI, Inc., Southborough, MA (US)

( * ) Notice: Subject to any disclaimer, the term of this patent is extended or adjusted under 35 U.S.C. 154(b) by 0 days.

(21) Appl. No.: 16/304,764

(22) PCT Filed: Jun. 10, 2016

(86) PCT No.: PCT/IB2016/053440
§ 371 (c)(1),
(2) Date: Nov. 27, 2018

(87) PCT Pub. No.: WO2017/212321
PCT Pub. Date: Dec. 14, 2017

(65) Prior Publication Data
US 2019/0336730 A1  Nov. 7, 2019

(51) Int. Cl.
*A61M 25/01* (2006.01)
*A61B 1/005* (2006.01)
*A61B 1/00* (2006.01)

(52) U.S. Cl.
CPC ....... *A61M 25/0136* (2013.01); *A61B 1/0052* (2013.01); *A61M 25/0147* (2013.01); *A61B 1/00135* (2013.01)

(58) Field of Classification Search
CPC .......... A61M 25/0136; A61M 25/0147; A61M 25/0133; A61M 25/0108; A61M 25/0141; A61B 1/0052; A61B 1/00135
See application file for complete search history.

(56) References Cited

U.S. PATENT DOCUMENTS

| | | | |
|---|---|---|---|
| 2002/0188278 A1 | 12/2002 | Tockman et al. | 604/527 |
| 2009/0156998 A1* | 6/2009 | Arana | A61M 25/0054 604/103 |

(Continued)

FOREIGN PATENT DOCUMENTS

| | | |
|---|---|---|
| JP | H 09-276212 A | 10/1997 |
| JP | 2007-151595 A | 6/2007 |

(Continued)

*Primary Examiner* — Emily L Schmidt
*Assistant Examiner* — Tiffany Legette
(74) *Attorney, Agent, or Firm* — Harrington & Smith (57) ABSTRACT

An apparatus includes a sheath configured to be at least partially inserted into a body of a patient, the sheath having a distal end and a proximal end; a housing coupled to the proximal end of the sheath; and a control mechanism operably coupled to the housing and slidable to move the sheath relative to the housing. The control mechanism includes a locking mechanism for locking the control mechanism in place relative to the housing; a deflection mechanism for articulating a distal end of the sheath; and a saddle slidable relative to the locking mechanism and the deflection mechanism. A device is coupled to the saddle and is extendable from and retractable within the sheath.

14 Claims, 7 Drawing Sheets

(56) References Cited

U.S. PATENT DOCUMENTS

2012/0184955 A1    7/2012   Pivotto et al. ................. 606/41
2016/0206853 A1*   7/2016   Bolduc ............. A61M 25/0147

FOREIGN PATENT DOCUMENTS

WO    WO 2012/039905 A1    3/2012
WO    WO 2013/147857 A1    10/2013
WO    WO 2014/093457 A1    6/2014

* cited by examiner

CONTROL MECHANISM FOR MEDICAL DEVICE

This patent application is a U.S. National Stage application of International Patent Application Number PCT/IB2016/053440 filed Jun. 10, 2016 which is hereby incorporated by reference in its entirety.

BACKGROUND

Technical Field

The exemplary and non-limiting embodiments disclosed herein relate generally to a control mechanism for a medical device insertable into a patient's body and, more particularly, to a mechanism for locking a medical device in a desired position and controlling movement of the medical device.

Brief Description of Prior Developments

WO2012039905A1 discloses a medical device for treatment of a sinus opening. WO2014093457A1 discloses a deflectable catheter having a steerable sheath.

SUMMARY

The following summary is merely intended to be exemplary. The summary is not intended to limit the scope of the claims.

In accordance with one aspect, an apparatus comprises a sheath configured to be at least partially inserted into a body of a patient, the sheath having a distal end and a proximal end; a housing coupled to the proximal end of the sheath; and a control mechanism operably coupled to the housing and slidable to move the sheath relative to the housing. The control mechanism comprises a locking mechanism for locking the control mechanism in place relative to the housing; a deflection mechanism for articulating a distal end of the sheath; and a saddle slidable relative to the locking mechanism and the deflection mechanism. A device is coupled to the saddle and is extendable from and retractable within the sheath.

In accordance with another aspect, a medical device for positioning a catheter having an expandable element comprises a handle having a control section slidable on the handle; a saddle slidable on the control section; and a steerable sheath coupled to the handle, the steerable sheath being configured to be inserted into a body of a patient and movable relative to the handle by sliding the control section. The control section comprises a locking stopper to lock the control section in place on the handle and an adjustment control to deflect a distal end of the steerable sheath. The catheter is positioned into the body of the patient by sliding movement of the saddle to move the catheter out of the steerable sheath.

In accordance with another aspect, a controlling assembly for a medical device has a handle and a steerable sheath coupled to the handle. The controlling assembly is slidable on the handle to extend the steerable sheath from the handle and comprises a locking mechanism to lock the controlling assembly to the handle and a deflection control mechanism connected to a distal end of the steerable sheath to control movement of the steerable sheath.

BRIEF DESCRIPTION OF THE DRAWINGS

The foregoing aspects and other features are explained in the following description, taken in connection with the accompanying drawings, wherein.

DETAILED DESCRIPTION OF EMBODIMENTS

Figure 1:
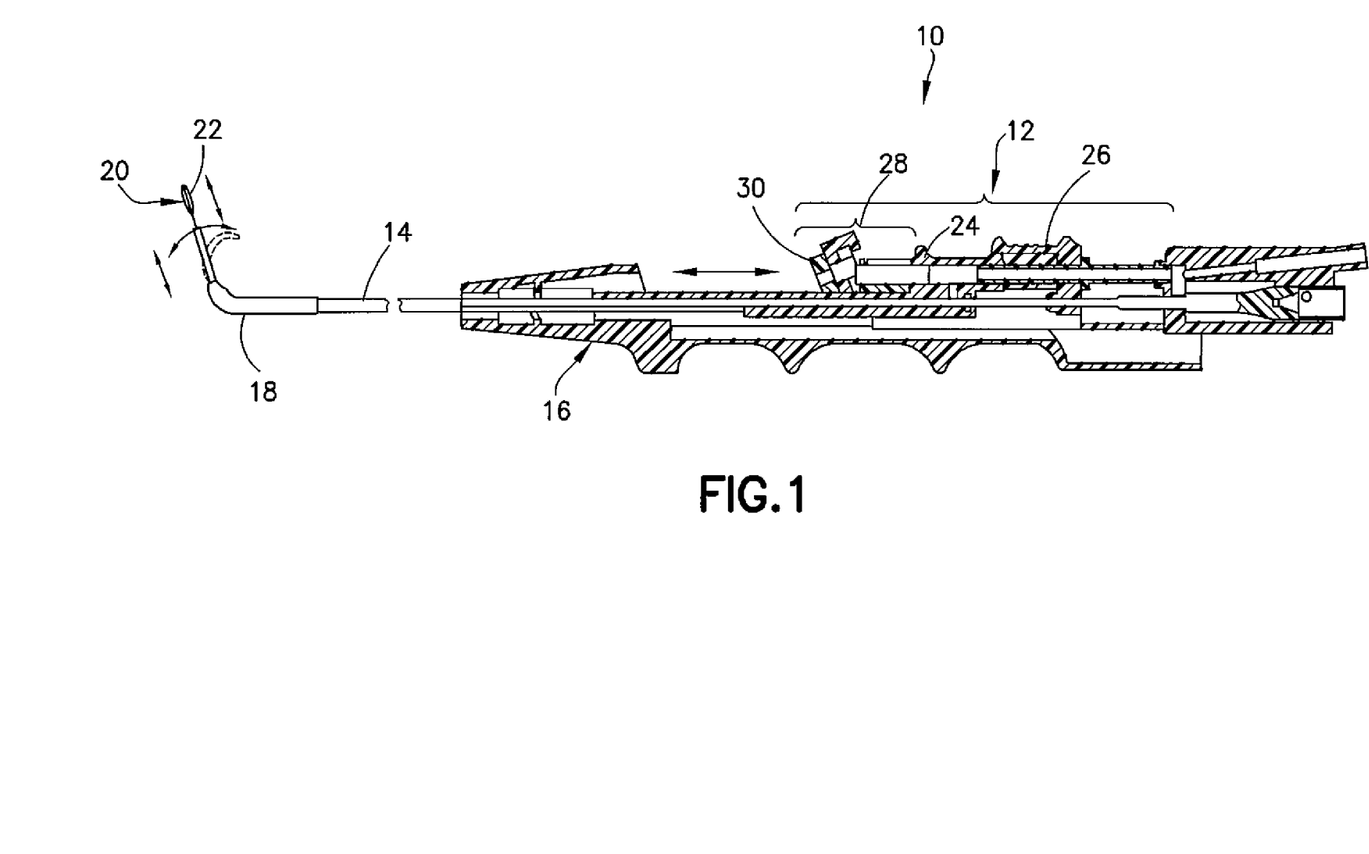
FIG. 1 is a partial cross-sectional side view of a medical device.

Referring to FIG. 1, one exemplary embodiment of an apparatus or medical device is designated generally by the reference number 10 and is hereinafter referred to as "device 10." Device 10, which may be configured to be partially inserted into a patient's body, such as through the patient's naris, for example, into the nasal ostium, and possibly to the sinus cavity, generally comprises a control section 12 and a steerable and deflectable flexible sheath 14 (e.g., plastic) connected to the control section 12 on a handle. The sheath 14 may be configured for the placement of a catheter, to provide access for an ocular device (e.g., for endoscopy), and/or to provide access for surgical instruments (e.g., for sinuplasty surgery). In one exemplary embodiment, the sheath 14 is manually steerable in the patient by manipulation of a steering wire connected to the control system 12, sliding movement of the control section 12, and rotational movement of the handle. The rotational movement of the handle produces a corresponding rotation of the distal end of the sheath 14 to allow the end of the sheath 14 to be directed accordingly.

In the device 10, the control section 12 is located in a housing 16 that forms the handle for the device 10. The sheath 14 extends from the housing 16 and includes an elbow 18 near a distal end of the sheath 14. The elbow 18 may be angled at any suitable angle (e.g., 70-90 degrees) to allow the sheath 14 to be directed in the patient's body. In the present examples, a balloon catheter 20 may be operably coupled to the control section 12 and positioned in the sheath 14 such that the balloon catheter 20 can be moved out of the distal end of the sheath 14 to allow a balloon 22 to be selectively inflated and deflated. The examples described herein are not limited to balloon catheters, however, as any type of catheter employing an expandable and collapsible device may be used in conjunction with the device 10. Additionally, devices such as scopes, lights, irrigation and suction tubes, surgical tools, data transfer cables, and the like may be positioned in the sheath 14. In some embodiments, the balloon catheter 20 may be positioned over such devices.

The control section 12 includes a slider 24 that slidably translates along the housing 16 and is lockable into position relative to the housing 16. The control section 12 also includes an accompanying saddle 26 slidably located rearward of the slider 24. The slider 24 includes a lock/deflector control system 28 to lock the slider 24 in position and to manipulate the distal end of the sheath 14. The lock/deflector control system 28 includes a locking stopper 30 to prevent movement of the slider 24 as well as a deflection adjustment control (shown at 50 in FIG. 4) to articulate movement at the distal end of the sheath 14. The saddle 26 receives the balloon catheter 20 (or other catheter) to allow an operator (e.g., a surgeon) to manually (e.g., by hand) extend and retract the balloon 22 relative to the sheath 14.

Figure 2:
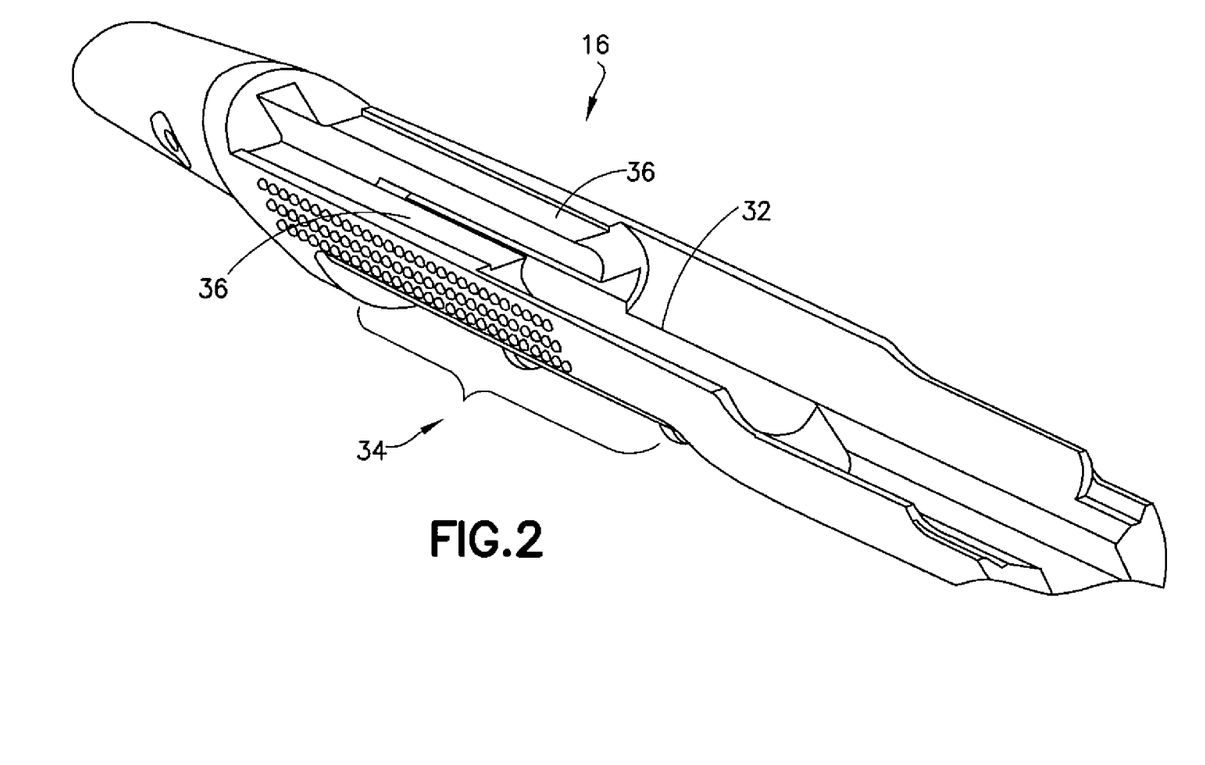
FIG. 2 is a perspective view of a housing for the medical device of FIG. 1.
Figure 3:
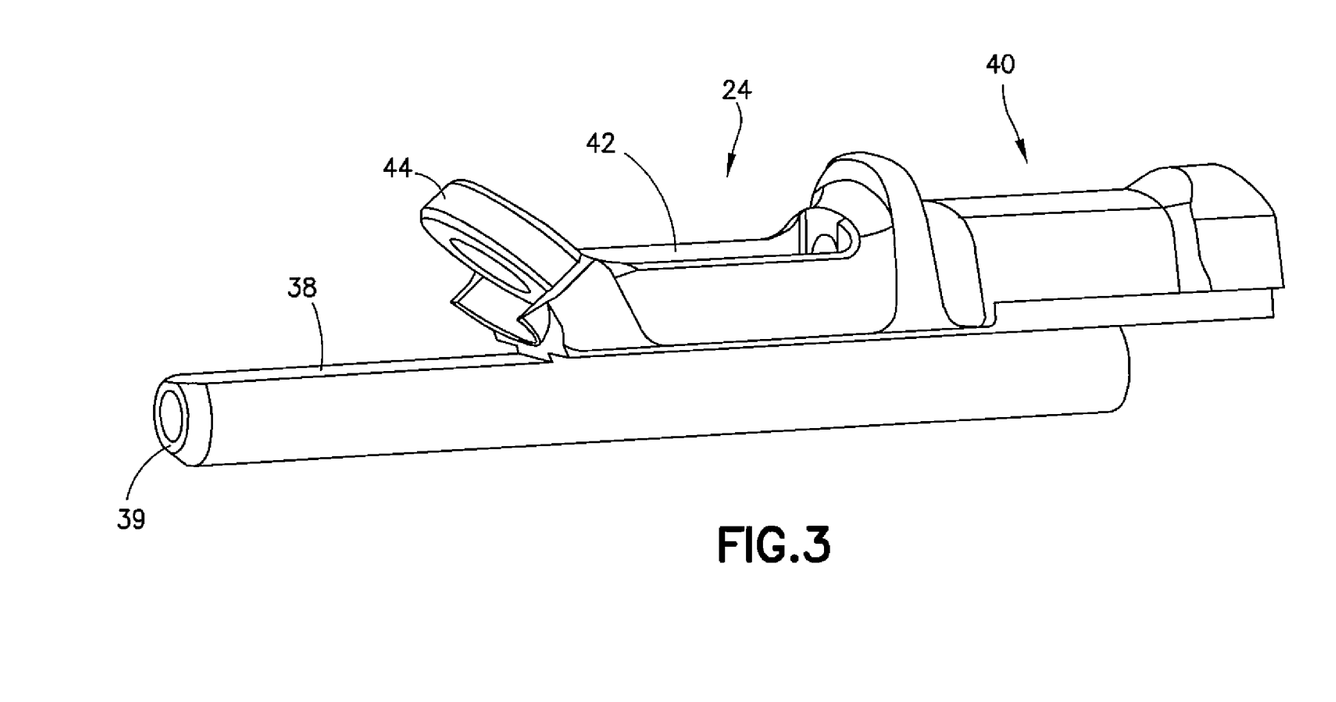
FIG. 3 is a perspective view of a slider for the medical device of FIG. 1.

Referring to FIGS. 2 and 3, in the example embodiment shown, the housing 16 as shown in FIG. 2 is an elongated element having an open top portion 32 and a closed bottom portion configured as a finger grip 34. The open top portion 32 includes rails 36 or similar structures protruding from opposing inside surfaces of the housing 16 along which the slider 24 translates. As shown in FIG. 3, the slider 24 comprises a barrel 38 and a frame 40 in which the lock/deflector control system 28 is mounted, the frame 40 being offset from a proximal end of the barrel 38 and comprising an open portion 42 forward of the saddle 26 in which the deflection adjustment control is mounted. The sheath 14 is received on a forward end 39 of the barrel 38. A ringlet 44 extends at an angle from a forward end of the frame 40 for housing the locking stopper 30 on the slider 24. The ringlet 44 may be circular, substantially circular, or of a polygonal shape (e.g., ten-sided or twelve-sided).

Figure 4:
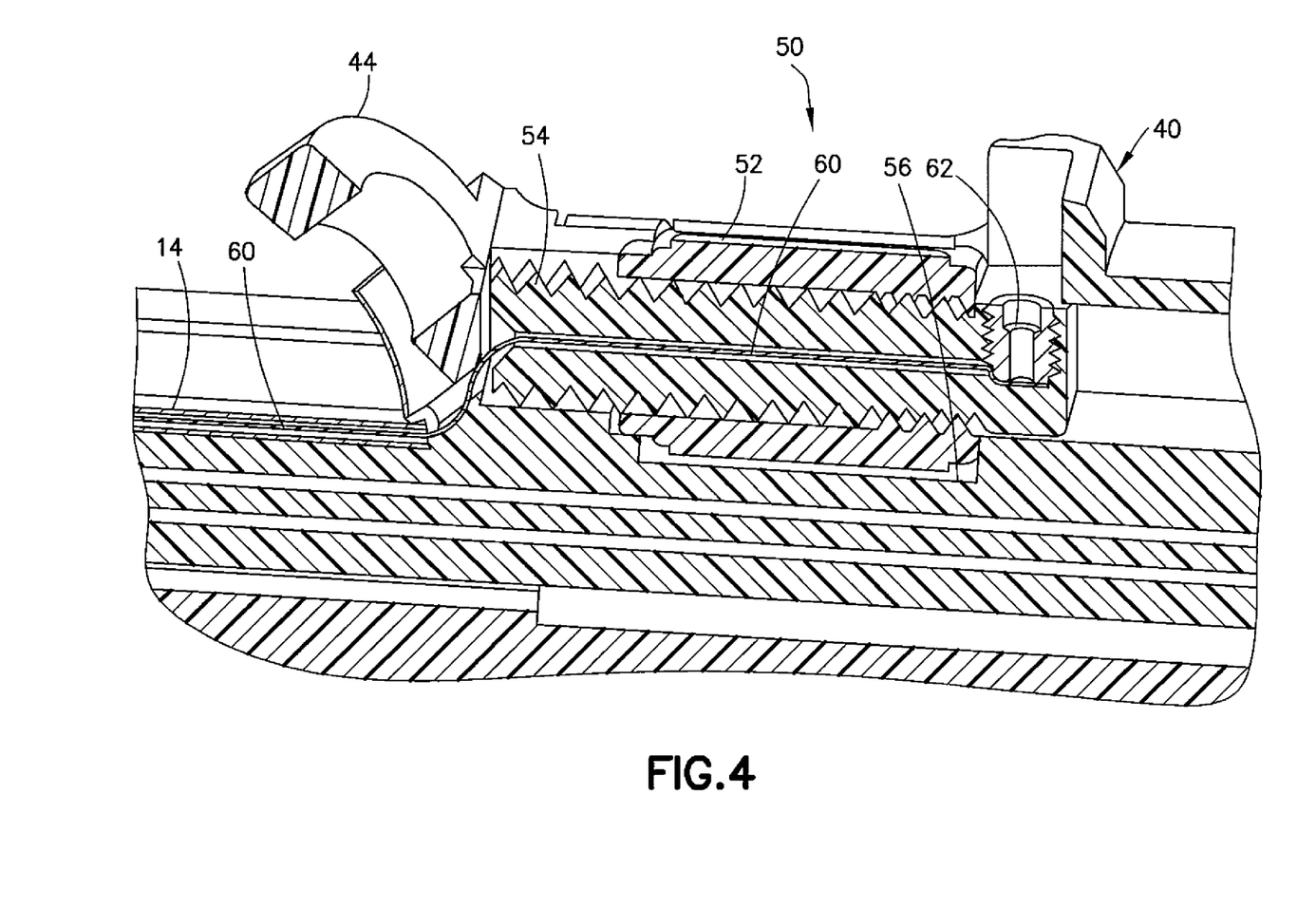
FIG. 4 is a cross-sectional view of a deflection adjustment control of the medical device.
Figure 5:
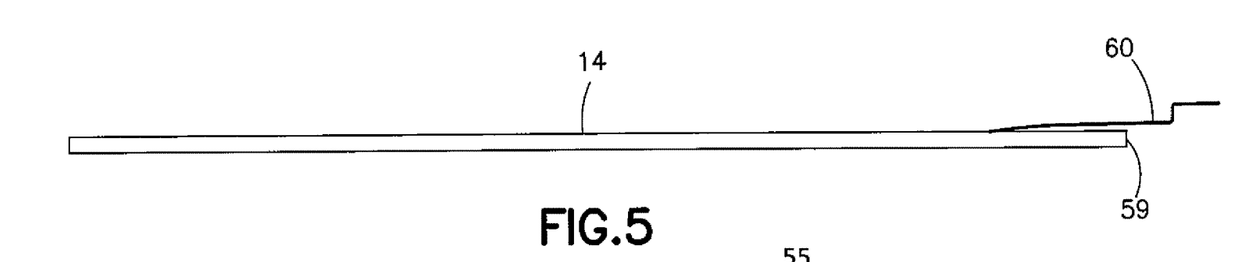
FIG. 5 is a perspective view of a sheath of the medical device receiving a deflection control wire.

Referring to FIG. 4, the deflection adjustment control 50 located in the frame 40 of the slider 24 comprises a dial roller 52 and a pitch screw 54 threadedly extending through the dial roller 52. The dial roller 52 is axially rotatable in a groove 56 or similar depression machined or otherwise formed in an upward facing surface of the slider 24 between the saddle 26 and the ringlet 44. The pitch screw 54 extends axially through the dial roller 52 such that rotation of the dial roller 52, which is captured in the frame 40 and maintained in place in the groove 56, causes forward and rearward translation of the pitch screw 54. A deflection control wire 60 (the steering wire) is connected to a rearward end of the pitch screw 54, for example, using a wire pinch screw 62 or other fastening means, and extends forward through the pitch screw 54, around the ringlet 44, and through a lumen in a wall of the sheath 14 to the distal end. The deflection control wire 60 is fixed to the distal end of the sheath 14. As shown in FIG. 5, the deflection control wire 60 may enter the lumen in the wall of the sheath 14 through a sidewall of the sheath 14. A proximal end 59 of the sheath 14 is coupled to the forward end 39 of the barrel 38.

Figure 6:
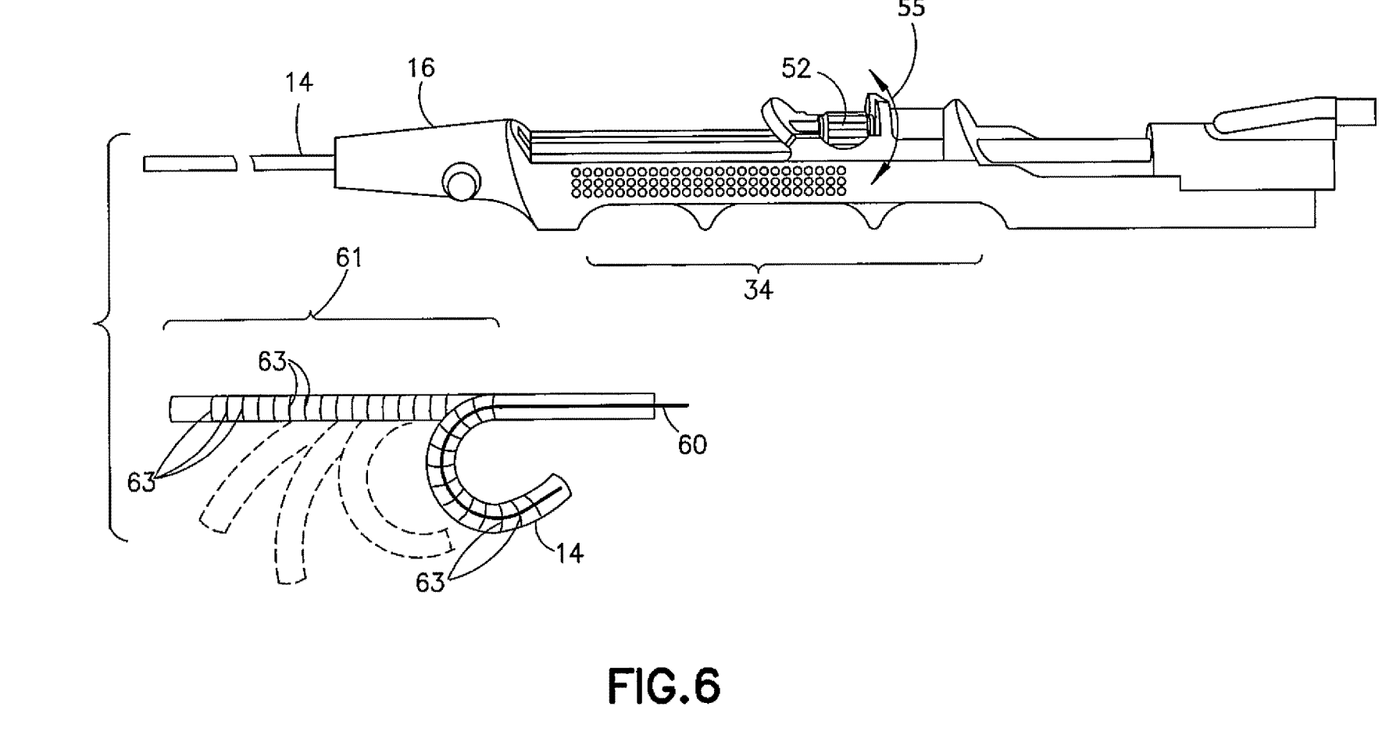
FIG. 6 is a side view the medical device of FIG. 1 illustrating deflection of a distal end of the sheath of the medical device.

Referring to FIG. 6, upon rotation of the dial roller 52 (shown by arrow 55) and translation of the pitch screw 54, the deflection control wire 60 is loosened or pulled to cause a portion 61 of the sheath 14 proximate the distal end of the sheath 14 to deflect. As can be seen, the end portion 61 of the sheath 14 is molded with grooves 63 or the like to impart flexibility to the distal end of the sheath 14, thereby allowing the sheath 14 to bend. The degree of deflection of the end portion 61 of the sheath 14 depends upon the configuration of the grooves 63 and the amount of travel of the pitch screw 54. Bending the sheath 14 is particularly useful for an ocular device such as a camera or other imaging device or a laser scanning device at the end of the sheath 14 to be turned to allow an operator to see, for example, the inside of a sinus cavity in order to visually confirm a condition of the sinus cavity.

Figure 7:
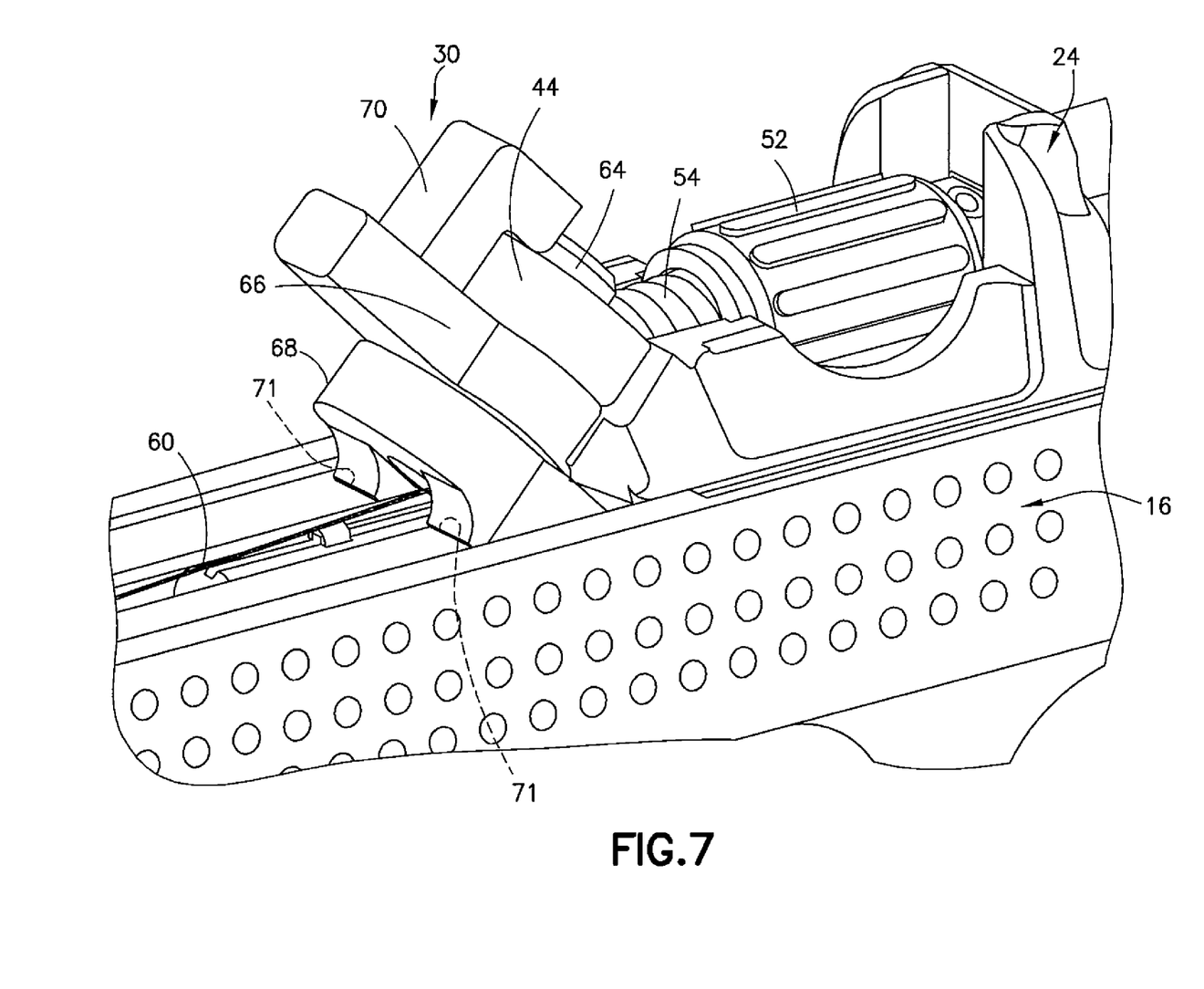
FIG. 7 is a perspective view of a lock/deflector control system of the medical device.
Figure 8:
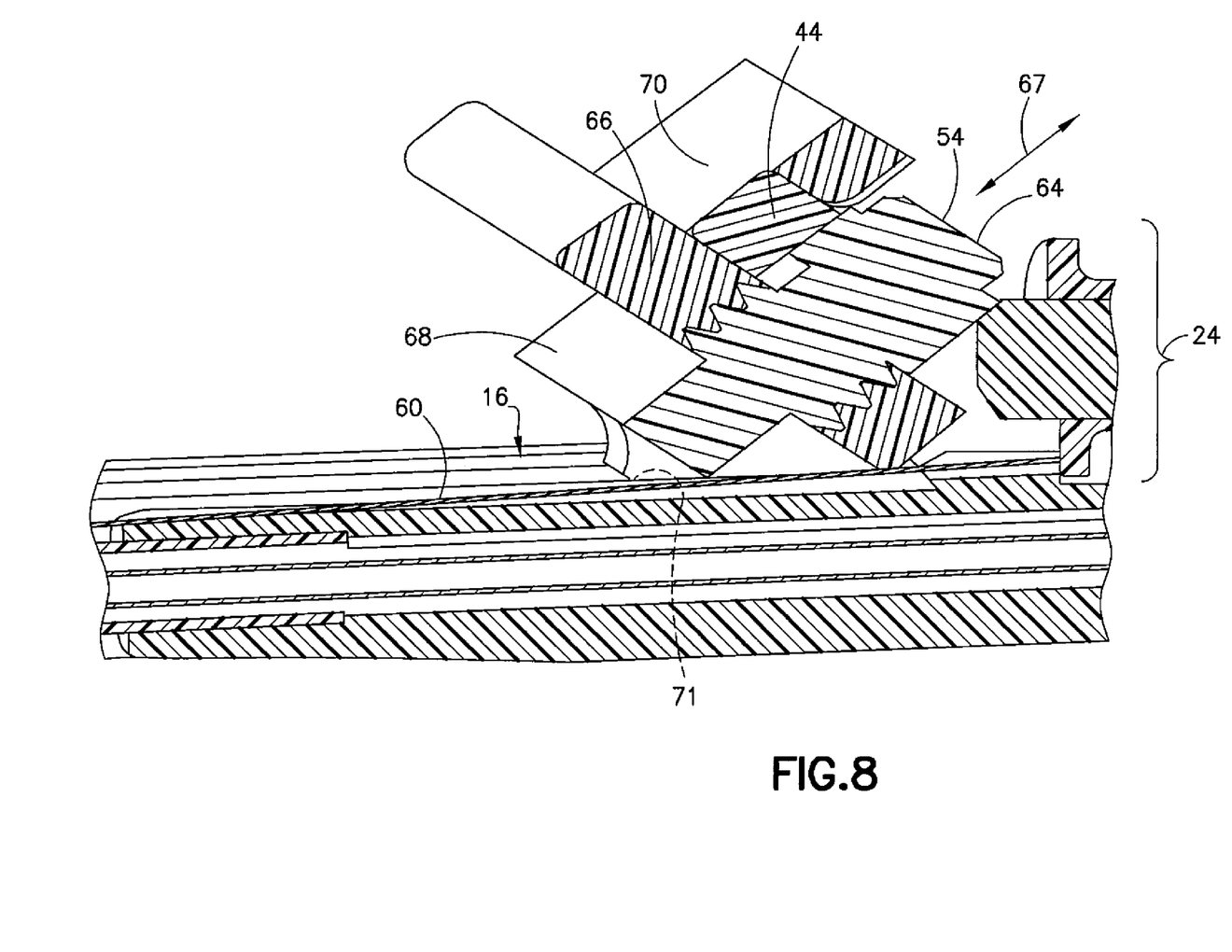
FIG. 8 is a cross-sectional view of the lock/deflector control system of FIG. 7.

Referring to FIGS. 7 and 8, the locking stopper 30 housed in the ringlet 44 comprises a screw 64, a threaded nut 66, and a shim plate 68. As can be seen in FIG. 7, the threaded nut 66 includes a finger control 70 extending from an outward-facing edge of the threaded nut 66. The threaded nut 66 and the finger control 70 may be one piece (e.g., integrally formed with each other). In the exemplary embodiment shown, the screw 64 is mounted into the ringlet 44 with the head of the screw facing upward and the threaded nut 66 threaded onto the screw 64 on the underside of the ringlet 44. The screw 64 may move relative to the ringlet 44 to allow the locking stopper 30 to control the movement between the slider 24 and the housing 16. In one example, the screw 64 and the shim plate 68 may be one component with the screw 64 fixed in place. In another example, the screw 64 and the shim plate 68 may be two parts, with the screw 64 and the shim plate 68 assembled into the ringlet 44 (e.g., due to assembly and manufacturing reasons). The shim plate 68 is bolted or otherwise coupled on an unthreaded end of the screw 64 on the underside of the threaded nut 66. As can be seen in FIG. 8, rotation of the threaded nut 66 by movement of the finger control 70 moves the screw 64 (as shown by arrow 67) and shim 68. In one exemplary embodiment, rotation of the finger control 70 from the left to the right would move the screw 64 in one direction to urge the shim plate 68 against surfaces 71 of the housing 16, thus providing a secure and firm stop and locking the slider 24 in place, whereas rotation of the finger control 70 from the right to the left would move the screw 64 in an opposing direction to loosen the shim plate 68 relative to the surfaces 71, thus allowing the slider 24 to be released and moved.

In this example, the deflection adjustment control 50 comprises the dial roller 52 and the pitch screw 54 such that rotating the dial roller 52 causes the pitch screw 54 to move forward or backward and correspondingly pull, loosen, or relax the deflection control wire 60 to articulate the end portion of the sheath 14. In an alternate example, the deflection adjustment control 50 may be a ball screw (to which the deflection control wire 60 is attached). For example, a ball screw with a pitch of about 0.160 inches per turn may allow for suitable movement of the deflection control wire 60 while minimizing the number of turns.

In any embodiment as disclosed herein, the balloon catheter 20 may be operably coupled to the slider 24 such that the balloon catheter 20 may be moved through the sheath 14 when the saddle 26 is manipulated. However, as the saddle 26 is pushed forward and the balloon catheter 20 is pushed into, for example, a narrow nasal ostium, the slider 24 may have a tendency to undesirably move, thus changing the position of the distal end of the sheath 14, due to one or more of friction between the balloon catheter 20 and inner surfaces of the sheath 14, resistance at the elbow 18, and resistance between the balloon 22 and walls of the nasal ostium (or other body part). In order to avoid such undesirable movement of the slider 24, the locking stopper 30 is tightened to firmly locate the slider 24 at any selected position along the housing 16 to ensure position accuracy between the sheath 14 and the balloon catheter 20 (or other device). Tightening the locking stopper 30 and firmly locating the slider 24 also allows for manipulation of the deflection adjustment control 50 without undesirable movement of the slider 24.

Although the features will be described with reference to the example embodiments of the control assembly shown in the drawings, it should be understood that features can be embodied in many alternate forms of embodiments. In addition, any suitable size, shape, or type of elements or materials could be used.

In one example, an apparatus comprises a sheath configured to be at least partially inserted into a body of a patient, the sheath having a distal end and a proximal end; a housing coupled to the proximal end of the sheath; and a control mechanism operably coupled to the housing and slidable to move the sheath relative to the housing. The control mechanism comprises a locking mechanism for locking the control mechanism in place relative to the housing; a deflection mechanism for articulating a distal end of the sheath; and a saddle slidable relative to the locking mechanism and the deflection mechanism. A device is coupled to the saddle and is extendable from and retractable within the sheath.

The locking mechanism may comprise a shim configured to be urged against the housing. The locking mechanism may further comprise a threaded nut and a screw, the screw being movable in an axial direction by an operator to urge the shim against the housing. The deflection mechanism may comprise a pitch screw and a deflection wire, a proximal end of the deflection wire being coupled to the pitch screw and a distal end of the deflection wire being coupled to the distal end of the sheath, the deflection wire being movable within a lumen in the sheath. The pitch screw may be operably coupled to a dial roller, the dial roller being configured to be manipulated to move the pitch screw relative to the housing and the sheath. The device coupled to the saddle may be a catheter. The catheter may be a balloon catheter.

In another example, a medical device for positioning a catheter having an expandable element comprises a handle having a control section slidable on the handle; a saddle slidable on the control section; and a steerable sheath coupled to the handle, the steerable sheath being configured to be inserted into a body of a patient and movable relative to the handle by sliding the control section. The control section comprises a locking stopper to lock the control section in place on the handle and an adjustment control to deflect a distal end of the steerable sheath. The catheter is positioned into the body of the patient by sliding movement of the saddle to move the catheter out of the steerable sheath.

The locking stopper may comprise a screw threadedly connected and movable in an axial direction to the control section at a first end of the screw, a threaded nut movable around a ringlet, and a shim plate bolted onto or otherwise coupled to a second end of the screw and configured to be urged against a surface of the handle. The adjustment control may comprise a pitch screw longitudinally movable along a length of the control section and a deflection wire connected between the pitch screw and the distal end of the steerable sheath. The medical device may further comprise a dial roller through which the pitch screw is positioned, the pitch screw being longitudinally movable along a length of the control section by rotation of the dial roller. The catheter may be a balloon catheter.

In another example, a controlling assembly for a medical device has a handle and a steerable sheath coupled to the handle. The controlling assembly is slidable on the handle to extend the steerable sheath from the handle and comprises a locking mechanism to lock the controlling assembly to the handle and a deflection control mechanism connected to a distal end of the steerable sheath to control movement of the steerable sheath.

The locking mechanism may comprise a screw, a threaded nut movable around a ringlet, and a shim plate bolted onto or otherwise coupled to an end of the screw and configured to be urged against the handle. The locking mechanism may further comprise the ringlet on a housing of the controlling assembly, the ringlet being configured to hold the screw. The deflection control mechanism may comprise a pitch screw longitudinally movable along a length of the controlling assembly and a deflection wire connected between the pitch screw and the distal end of the steerable sheath. The controlling assembly may further comprise a roller through which the pitch screw is received, the roller being rollable to cause the pitch screw to translate therethrough to pull or loosen the deflection wire. The controlling assembly may further comprise a wire pinch screw positioned at a proximal end of the controlling assembly to fasten the deflection wire to the pitch screw.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications, and variances which fall within the scope of the appended claims.

What is claimed is:

1. An apparatus, comprising:
   a sheath configured to be at least partially inserted into a body of a patient, the sheath having a distal end and a proximal end;
   a housing coupled to the proximal end of the sheath; and
   a control mechanism operably coupled to the housing and slidable to move the sheath relative to the housing, the control mechanism comprising:
   a locking mechanism for locking the control mechanism in place relative to the housing;
   a deflection mechanism for articulating a distal end of the sheath; and
   a saddle slidable relative to the locking mechanism and the deflection mechanism;
   wherein a device is coupled to the saddle and is extendable from and retractable within the sheath;
   wherein the locking mechanism comprises a shim configured to be urged against the housing; and
   wherein the locking mechanism further comprises a threaded nut and a screw, the screw being movable in an axial direction by an operator to urge the shim against the housing.

2. The apparatus of claim 1, wherein the deflection mechanism comprises a pitch screw and a deflection wire, a proximal end of the deflection wire being coupled to the pitch screw and a distal end of the deflection wire being coupled to the distal end of the sheath, the deflection wire being movable within a lumen in the sheath.

3. The apparatus of claim 2, wherein the pitch screw is operably coupled to a dial roller, the dial roller being configured to be manipulated to move the pitch screw relative to the housing and the sheath.

4. The apparatus of claim 1, wherein the device coupled to the saddle is a catheter.

5. The apparatus of claim 4, wherein the catheter is a balloon catheter.

6. A medical device for positioning a catheter having an expandable element, the medical device comprising:
   a handle having a control section slidable on the handle;
   a saddle slidable on the control section; and
   a steerable sheath coupled to the handle, the steerable sheath being configured to be inserted into a body of a patient and movable relative to the handle by sliding the control section;
   the control section comprising,
   a locking stopper to lock the control section in place on the handle, and
   an adjustment control to deflect a distal end of the steerable sheath;
   wherein sliding movement of the saddle positions the catheter out of the steerable sheath and into the body of the patient; and wherein the locking stopper comprises,
a screw threadedly connected and movable in an axial direction to the control section at a first end of the screw,
a threaded nut movable around a ringlet, and
a shim plate bolted onto a second end of the screw and configured to be urged against a surface of the handle.

7. The medical device of claim 6, wherein the sliding movement of the saddle positions a balloon catheter.

8. The medical device of claim 6, wherein the adjustment control comprises,
a pitch screw longitudinally movable along a length of the control section, and
a deflection wire connected between the pitch screw and the distal end of the steerable sheath.

9. The medical device of claim 8, further comprising a dial roller through which the pitch screw is positioned, the pitch screw being longitudinally movable along a length of the control section by rotation of the dial roller.

10. A controlling assembly for a medical device having a handle and a steerable sheath coupled to the handle, the controlling assembly being slidable on the handle to extend the steerable sheath from the handle, the controlling assembly comprising:
a locking mechanism to lock the controlling assembly to the handle; and
a deflection control mechanism connected to a distal end of the steerable sheath to control movement of the steerable sheath;
wherein the locking mechanism comprises a screw, a threaded nut movable around a ringlet, and a shim plate bolted onto an end of the screw and configured to be urged against the handle.

11. The controlling assembly of claim 10, wherein the locking mechanism further comprises the ringlet on a housing of the controlling assembly, the ringlet being configured to hold the screw.

12. The controlling assembly of claim 10, wherein the deflection control mechanism comprises a pitch screw longitudinally movable along a length of the controlling assembly, and a deflection wire connected between the pitch screw and the distal end of the steerable sheath.

13. The controlling assembly of claim 12, further comprising a roller through which the pitch screw is received, the roller being rollable to cause the pitch screw to translate therethrough to pull or loosen the deflection wire.

14. The controlling assembly of claim 12, further comprising a wire pinch screw positioned at a proximal end of the controlling assembly to fasten the deflection wire to the pitch screw.

* * * * *